United States Patent [19]
Hayes

[11] 3,980,726
[45] Sept. 14, 1976

[54] DEHYDROGENATION WITH A NONACIDIC MULTIMETALLIC CATALYST

[75] Inventor: John C. Hayes, Palatine, Ill.

[73] Assignee: Universal Oil Products Company, Des Plaines, Ill.

[22] Filed: Dec. 20, 1974

[21] Appl. No.: 535,078

Related U.S. Application Data

[63] Continuation-in-part of Ser. No. 365,877, June 1, 1973, Pat. No. 3,856,870, which is a continuation-in-part of Ser. No. 27,457, April 10, 1970, abandoned.

[52] U.S. Cl. .................. 260/668 D; 260/669 R; 260/683.3; 208/138
[51] Int. Cl.$^2$ ................ C07C 15/10; C07C 3/34; C07C 5/40
[58] Field of Search ............ 260/668 D, 669, 683.3; 208/138

[56] References Cited
UNITED STATES PATENTS

| | | | |
|---|---|---|---|
| 3,649,565 | 3/1972 | Wilhelm | 260/668 D |
| 3,686,340 | 8/1972 | Patrick et al. | 208/138 |
| 3,755,480 | 8/1973 | Wilhelm | 260/668 D |
| 3,827,988 | 8/1974 | Konimani et al. | 260/668 D |
| 3,856,870 | 12/1974 | Hayes | 260/669 R |

*Primary Examiner*—D. Horwitz
*Attorney, Agent, or Firm*—James R. Hoatson, Jr.; Thomas K. McBride; William H. Page, II

[57] ABSTRACT

Dehydrogenatable hydrocarbons are dehydrogenated by contacting them at dehydrogenation conditions with a nonacidic catalytic composite comprising a combination of catalytically effective amounts of a platinum or palladium component, an iridium component, a tin or lead component, and an alkali or alkaline earth component with a porous carrier material. A specific example of the nonacidic, multimetallic catalytic composite disclosed herein is a combination of a platinum component, an iridium component, a tin or lead component, and an alkali or alkaline earth component with an alumina carrier material. The amounts of the catalytically active components contained in this last composite are, on an elemental basis, 0.01 to 2 wt. % platinum, 0.01 to 2 wt. % iridium, 0.01 to 5 wt. % tin or lead, and 0.1 to 5 wt. % of the alkali or alkaline earth metal.

14 Claims, No Drawings

Н3,980,726

DEHYDROGENATION WITH A NONACIDIC MULTIMETALLIC CATALYST

CROSS-REFERENCES TO RELATED APPLICATIONS

This application is a continuation-in-part of my prior, copending application Ser. No. 365,877 filed June 1, 1973, now Pat. No. 3,856,870, Dec. 24, 1974, which in turn is a continuation-in-part of my prior, now abandoned, application Ser. No. 27,457 filed Apr. 10, 1970. All of the teachings of these prior applications are specifically incorporated herein by reference.

The subject of the present invention is, broadly, an improved method for dehydrogenating a dehydrogenatable hydrocarbon to produce a product hydrocarbon containing the same number of carbon atoms but fewer hydrogen atoms. In a narrower aspect, the present invention is a method of dehydrogenating normal paraffin hydrocarbons containing 4 to 30 carbon atoms per molecule to the corresponding normal mono-olefins with minimum production of side products. Another aspect of the present invention involves a novel non-acidic, multimetallic catalytic composite comprising a combination of catalytically effective amounts of a platinum or palladium component, an iridium component, a tin or lead component, and an alkali or alkaline earth metal component with a porous carrier material. This composite has highly preferred characteristics of activity, selectivity, and stability when it is employed in the dehydrogenation of dehydrogenatable hydrocarbons such as aliphatic hydrocarbons, naphthenic hydrocarbons, and alkylaromatic hydrocarbons.

The dehydrogenation of dehydrogenatable hydrocarbons is an important commercial process because of the great and expanding demand for dehydrogenated hydrocarbons for use in the manufacture of various chemical products such as detergents, plastics, synthetic rubbers, pharmaceutical products, high octane gasoline, perfumes, drying oils, ion-exchanged resins, and various other products well known to those skilled in the art. One example of this demand is in the manufacture of high octane gasoline by using $C_3$ and $C_4$ mono-olefins to alkylate isobutane. A second example is the greatly increased requirements of the petrochemical industry for the production of aromatic hydrocarbons from the naphthene component of petroleum. Another example of this demand is in the area of dehydrogenation of normal paraffin hydrocarbons to produce normal mono-olefins having 4 to 30 carbon atoms per molecule. These normal mono-olefins can, in turn, be utilized in the synthesis of vast numbers of other chemical products. For example, derivatives of normal mono-olefins have become of substantial importance to the detergent industry where they are utilized to alkylate an alkylatable aromatic such as benzene, with subsequent transformation of the product arylalkane into a wide variety of biodegradable detergents such as the alkylaromatic sulfonate type of detergent which is most widely used today for household, industrial, and commercial purposes. Still another large class of detergents produced from these normal mono-olefins are the oxyalkylated phenol derivatives in which the alkyl phenol base is prepared by the alkylation of phenol with these normal mono-olefins. Yet another type of detergent produced from these normal mono-olefins is a biodegradable alkylsulfate formed by the direct sulfation of the normal mono-olefin. Likewise, the olefin can be subjected to direct sulfonation to make biodegradable alkenylsulfonates. As a further example, these mono-olefins can be hydrated to produce alcohols which then, in turn can be used to produce plasticizers, synthetic lube oils and the like products.

Regarding the use of products made by the dehydrogenation of alkylaromatic hydrocarbons, these find wide application in industries including the petroleum, petrochemical, pharmaceutical, detergent, plastic industries, and the like. For example, ethylbenzene is dehydrogenated to produce styrene which is utilized in the manufacturing of polystyrene plastics, styrene-butadiene rubber, and the like products. Isopropylbenzene is dehydrogenated to form alphamethyl styrene which, in turn, is extensively used in polymer formation and in the manufacture of drying oils, ion-exchange resins, and the like material.

Responsive to this demand for these dehydrogenation products, the art has developed a number of alternative methods to produce them in commercial quantities. One method that is widely utilized involves the selective dehydrogenation of dehydrogenatable hydrocarbons by contacting the hydrocarbons with a suitable catalyst at dehydrogenation conditions. As is the case with most catalytic procedures, the principal measure of effectiveness for this dehydrogenation method involves the ability to perform its intended function with minimum interference of side reactions for extended periods of time. The analytical terms used in the art to broadly measure how well a particular catalyst performs its intended functions in a particular hydrocarbon conversion reaction are activity, selectivity, and stability, and for purposes of discussion here these terms are generally defined for a given reactant as follows: (1) activity is a measure of the catalyst's ability to convert the hydrocarbon reactant into products at a specified severity level where severity level means the conditions used — that is, the temperature, pressure, contact time, and presence of diluents such as $H_2$; (2) selectivity usually refers to the amount of desired product or products obtained relative to the amount of the reactant charged or converted; (3) stability refers to the rate of change with time of the activity and selectivity parameters — obviously the smaller rate implying the more stable catalyst. More specifically, in a dehydrogenation process, activity commonly refers to the amount of conversion that takes place for a given dehydrogenatable hydrocarbon at a specified severity level and is typically measured on the basis of disappearance of the dehydrogenatable hydrocarbon; selectivity is typically measured by the amount, calculated on a mole percent of converted dehydrogenatable hydrocarbon basis, of the desired dehydrogenated hydrocarbon obtained at the particular activity or severity level; and stability is typically equated to the rate of change with time of activity as measured by disappearance of the dehydrogenatable hydrocarbon and of selectivity as measured by the amount of desired hydrocarbon produced. Accordingly, the major problem facing workers in the hydrocarbon dehydrogenation art is the development of a more active and selective catalytic composite that has good stability characteristics.

I have now found a nonacidic multimetallic catalytic composite which possesses improved activity, selectivity, and stability characteristics when it is employed in a process for the dehydrogenation of dehydrogenatable hydrocarbons. In particular, I have determined that a superior dehydrogenation catalyst comprises a nonacidic combination of catalytically effective amounts of a platinum or palladium component, an iridium component, a tin or lead component, and an alkali or alkaline earth component with a porous carrier material in a manner such that the components are uniformly dispersed throughout the porous carrier material, the platinum or palladium and iridium components are reduced to the corresponding elemental state and the tin or lead component and the alkali or alkaline earth component are both present in positive oxidation states. This catalyst can, in turn, enable the performance of a dehydrogenation process to be substantially improved. Moreover, particularly good results are obtained when this nonacidic multimetallic catalyst is utilized in the dehydrogenation of long chain normal paraffins to produce the corresponding normal monoolefins with minimization of side reactions such as skeletal isomerization, aromatization, and cracking. In sum, the current invention involves the significant finding that a combination of specially selected amounts of an iridium component and a tin or lead component can be utilized to beneficially interact with a platinum- or palladium-containing nonacidic dehydrogenation catalyst if the metal moieties are uniformly dispersed in the catalyst and if their oxidation states are controlled as hereinafter specified.

It is, accordingly, one object of the present invention to provide a novel method for dehydrogenation of dehydrogenatable hydrocarbons utilizing a nonacidic multimetallic catalytic composite containing specially selected amounts of a platinum or palladium component, an iridium component, a tin or lead component, and an alkali or alkaline earth component combined with a porous carrier material. A second object is to provide a novel nonacidic catalytic composite having superior performance characteristics when utilized in a dehydrogenation process. Another object is to provide an improved method for the dehydrogenation of normal paraffins to produce normal mono-olefins. Yet another object is to improve the performance of a nonacidic platinum- or palladium-containing dehydrogenation catalyst by using a combination of components, iridium and tin or lead, to beneficially interact and promote the platinum or palladium metal.

In brief summary, one embodiment of the present invention involves a nonacidic catalytic composite comprising a porous carrier material containing, on an elemental basis, about 0.01 to about 2 wt. % platinum or palladium, about 0.01 to about 2 wt. % iridium, about 0.01 to about 5 wt. % tin or lead, and about 0.01 to about 5 wt. % of an alkali or alkaline earth metal, wherein the platinum or palladium, tin or lead, iridium, and alkali or alkaline earth metal components are uniformly dispersed throughout the porous carrier material, wherein substantially all of the platinum or palladium and iridium components are present in the corresponding elemental metallic states, wherein substantially all of the tin or lead component is present in an oxidation state above that of the elemental metal and wherein substantially all of the alkali or alkaline earth metal component is present in an oxidation state above that of the elemental metal.

A second more specific embodiment relates to a nonacidic catalytic composite comprising an alumina carrier material containing, on an elemental basis, about 0.05 to about 1 wt. % platinum or palladium, about 0.05 to about 1 wt. % iridium, about 0.05 to about 2 wt. % tin or lead, and about 0.25 to about 3.5 wt. % alkali or alkaline earth metal, wherein the platinum or palladium, tin or lead, iridium, and alkali or alkaline earth metal components are uniformly dispersed throughout the alumina carrier material, wherein substantially all of the platinum or palladium and iridium components are present in the corresponding elemental metallic states; wherein substantially all of the tin or lead component is present in an oxidation state above that of the elemental metal and wherein substantially all of the alkali or alkaline earth metal component is present in an oxidation state above that of the elemental metal.

A third embodiment comprehends a method for dehydrogenating a dehydrogenatable hydrocarbon which essentially involves contacting the dehydrogenatable hydrocarbon at dehydrogenation conditions with the nonacidic multimetallic catalytic composite defined above in the first or second embodiment.

Another embodiment involves a method for the selective dehydrogenation of a normal paraffin hydrocarbon containing about 4 to 30 carbon atoms per molecule to the corresponding normal mono-olefins. The method essentially involves contacting the normal paraffin hydrocarbon and hydrogen at dehydrogenation conditions with a catalytic composite of the type defined above in the first or second embodiment.

Other objects and embodiments of the present invention include specific details regarding essential and preferred ingredients of the disclosed multimetallic catalytic composite, preferred amounts of ingredients for this composite, suitable methods of composite preparation, dehydrogenatable hydrocarbons that are preferably used with this catalyst in a dehydrogenation process, operating conditions that can be utilized with this catalyst in a dehydrogenation process and the like particulars. These objects and embodiments are disclosed in the following detailed explanation of the various technical aspects of the present invention. It is to be noted that: (1) the terms "catalyst" and "catalytic composite" are used herein in an equivalent and interchangeable manner; (2) the expression "uniformly dispersed throughout a carrier material" is intended to mean that the concentration of the component is approximately the same in any reasonably divisible portion of the carrier material; and, (3) the term "nonacidic" means that the catalyst produces less then 10% conversion of 1-butene to isobutylene when tested at dehydrogenation conditions, and preferably less than 1%.

Regarding the dehydrogenatable hydrocarbon that is subjected to the instant method, it can, in general, be an organic compound having 2 to 30 carbon atoms per molecule and containing at least 1 pair of adjacent carbon atoms having hydrogen attached thereto. That is, it is intended to include within the scope of the present invention the dehydrogenation of any organic compound capable of being dehydrogenated to produce products containing the same number of carbon atoms but fewer hydrogen atoms, and capable of being vaporized at the dehydrogenation conditions used herein. More particularly, suitable dehydrogenatable hydrocarbons are: aliphatic compounds containing 2 to 30 carbon atoms per molecule, alkylaromatic hydrocarbons where the alkyl group contains 2 to 6 carbon atoms, and naphthenes or alkyl-substituted naphthenes. Specific examples of suitable dehydrogenatable hydrocarbons are: (1) alkanes such as ethane, propane, n-butane, isobutane, n-pentane, isopentane, n-hexane, 2-methylpentane, 2,2-dimethylbutane, n-heptane, n-octane, 2-methylhexane, 2,2,3-trimethylbutane, and the like compounds; (2) naphthenes such as cyclopentane, methylcyclopentane, ethylcyclopentane, n-propylcyclopentane, cyclohexane, isopropylcyclopentane, 1,3-dimethylcyclohexane, and the like compounds; and (3) alkylaromatics such as ethylbenzene, n-propylbenzene, n-butylbenzene, 1,3,5-triethylbenzene, isopropylbenzene, isobutylbenzene, ethylnaphthalene, and the like compounds.

In a preferred embodiment, the dehydrogenatable hydrocarbon is a normal paraffin hydrocarbon having about 4 to about 30 carbon atoms per molecule. For example, normal paraffin hydrocarbons containing about 10 to 18 carbon atoms per molecule are dehydrogenated by the subject method to produce the corresponding normal mono-olefin which can, in turn, be alkylated with benzene and sulfonated to make alkylbenzene sulfonate detergents having superior biodegradability. Likewise, n-alkanes having 10 to 18 carbon atoms per molecule can be dehydrogenated to the corresponding normal mono-olefin which, in turn, can be sulfated or sulfonated to make excellent detergents. Similarly, n-alkanes having 6 to 10 carbon atoms per molecule can be dehydrogenated to form the corresponding mono-olefins which can, in turn, be hydrated to produce valuable alcohols. Preferred feed streams for the manufacture of detergent intermediates contain a mixture of 4 or 5 adjacent normal paraffin homologues such as $C_{10}$ to $C_{13}$, $C_{11}$ to $C_{14}$, $C_{11}$ to $C_{15}$, and the like mixtures.

An essential feature of the present invention involves the use of a nonacidic multimetallic catalytic composite comprising a combination of catalytically effective amounts of a platinum or palladium component, an iridium component, a tin or lead component, and an alkali or alkaline earth component with a porous carrier material.

Considering first the porous carrier material, is is preferred that the material be a porous, adsorptive, high surface area support having a surface area of about 25 to about 500 $m^2/g$. The porous carrier material should be relatively refractory to the conditions utilized in the dehydrogenation process and it is intended to include within the scope of the present invention carrier materials which have traditionally been utilized in hydrocarbon conversion catalysts such as: (1) activated carbon, coke, or charcoal; (2) silica or silica gel, silicon carbide, clays, and silicates including those synthetically prepared and naturally occurring, which may or may not be acid treated for example, attapulgus clay, china clay, diatomacous earth, fuller's earth, kaolin, kieselguhr, etc.; (3) ceramics, porcelain, crushed firebrick, bauxite, (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; and, (6) combination of elements from one or more of these groups. The preferred porous carrier materials for use in the present invention are refractory inorganic oxides, with best results obtained with an alumina carrier material. Suitable alumina materials are the crystalline aluminas known as the gamma-, eta-, and theta-aluminas, with gamma-alumina giving best results. In addition, in some embodiments, the alumina carrier material may contain minor proportions of other well known refractory inorganic oxides such as silica, zirconia, magnesia, etc.; however, the preferred support is substantially pure gamma-alumina. Preferred carrier materials have an apparent bulk density of about 0.3 to about 0.7 g/cc and surface area characteristics such that the average pore diameter is about 20 to 300 Angstroms, the pore volume is about 0.1 to 1 cc/g and the surface area is about 100 to about 500 $m^2/g$. In general, excellent results are typically obtained with a gamma-alumina carrier material which is used in the form of spherical particles having: a relatively small diameter (i.e. typically about 1/16 inch), an apparent bulk density of about 0.5 g/cc, a pore volume of about 0.5 cc/g, and a surface area of about 175 $m^2/g$.

The preferred alumina carrier material may be prepared in any suitable manner and may be synthetically prepared or natural occurring. Whatever type of alumina is employed it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying the calcining is converted to alumina. The alumina carrier may be formed in any desired shape such as spheres, pills, cakes, extrudates, powders, granules, etc., and utilized in any desired size. For the purpose of the present invention a particularly preferred form of alumina is the sphere; and alumina spheres may be continuously manufactured by the well-known oil drop method which comprises; forming an alumina hydrosol by any of the techniques taught in the art and preferably by reacting aluminum metal with hydrochloric acid; combining the resulting hydrosol with a suitable gelling agent; and dropping the resultant mixture into an oil bath maintained at elevated temperatures. The droplets of the mixture remain in the oil bath until they set and form hydrogen spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300°F. to about 400°F. and subjected to a calcination procedure at a temperature of about 850°F. to about 1300°F. for a period of about 1 to 20 hours. It is a good practice to subject the calcined particles to a high temperature treatment with steam in order to remove undesired acidic components such as any residual chloride. This method effects conversion of the alumina hydrogel to the corresponding crystalline gamma-alumina. See the teachings of U.S. Pat. No. 2,620,314 for additional details.

One essential constituent of the instant multimetallic catalytic composite is the tin or lead component. It is an essential feature of the present invention that substantially all of the tin or lead component is present in the final catalyst in an oxidation state above that of the elemental metal. In other words, this component may be present in chemical combination with one or more of the other ingredients of the composite, or as a chemical compound of tin or lead such as the oxide, sulfide, halide, oxyhalide, oxychloride, aluminate, and the like compounds. Based on the evidence currently available, it is believed that best results are obtained when substantially all of the tin or lead component exists in the final composite in the form of the corresponding oxide such as the tin oxide or lead oxide, and the subsequently described oxidation and reduction steps, that are preferably used in the preparation of the instant composite, are believed to result in a catalytic composite which contains an oxide of the tin or lead component. Regardless of the state in which this component exists in the composite, it can be utilized therein in any amount which is catalytically effective, with the preferred amount being about 0.01 to about 5 wt. % thereof, calculated on an elemental basis and the most preferred amount being about 0.05 to about 2 wt. %. The exact amount selected within this broad range is preferably determined as a function of the particular metal that is utilized. For instance, in the case where this component is lead, it is preferred to select the amount of this component from the low end of this range—namely, about 0.01 to about 1 wt. %. Additionally, it is preferred to select the amount of lead as a function of the amount of the platinum group component as explained hereinafter. On the other hand, where this component is tin, it is preferred to select from a relatively broader range of about 0.05 to about 2 wt. % thereof. It is to be understood that mixtures of tin and lead are intended to be included within the scope of the expression "tin or lead component".

This tin or lead component may be incorporated in the composite in any suitable manner known to the art to result in a uniform dispersion of the tin or lead moiety throughout the carrier material such as, coprecipitation or cogellation with the porous carrier material, ion exchange with the carrier material, or impregnation of the carrier material at any stage in its preparation. It is to be noted that it is intended to include within the scope of the present invention all conventional procedures for incorporating a metallic component in a catalytic composite, and the particular method of incorporation used is not deemed to be an essential feature of the present invention so long as the tin or lead component is uniformly distributed throughout the porous carrier material. One acceptable method of incorporating the tin or lead component into the catalytic composite involves cogelling the tin or lead component during the preparation of the preferred carrier material, alumina. This method typically involves the addition of a suitable soluble compound of the tin or lead to the alumina hydrosol. The resulting mixture is then commingled with a suitable gelling agent, such as a relatively weak alkaline reagent, and the resulting mixture is thereafter preferably gelled by dropping into a hot oil bath as explained hereinbefore. After aging, drying, and calcining the resulting particles there is obtained an intimate combination of the oxide of the tin or lead and alumina. One preferred method incorporating this component into the composite involves utilization of a soluble decomposable compound of the tin or lead to impregnate the porous carrier material either before, during, or after the carrier material is calcined. In general, the solvent used during this impregnation step is selected on the basis of its capability to dissolve the desired tin or lead compound without affecting the porous carrier material which is to be impregnated; ordinarily, good results are obtained when water is the solvent; thus the preferred tin or lead compounds for use in this impregnation step are typically water-soluble and decomposable. Examples of suitable tin or lead compounds are: ammonium chlorostannate, tin dichloride, tin tetrachloride, tin dibromide, tin dibromide di-iodide, tin tetrafluoride, tin tetraiodide, tin sulfate, tin tartrate, diethyltin dichloride, lead diacetate, lead dibromate, lead dibromide, lead dichlorate, lead dichloride, lead dicitrate, lead diformate, lead dilactate, lead malate, lead dinitrate, lead nitrite, lead dithionate, and the like compounds. In the case of tin, tin di- or tetra-chloride dissolved in water is preferred. In the case of lead, lead nitrate dissolved in water is preferred. Regardless of which impregnation solution is utilized, the tin or lead component can be impregnated either prior to, simultaneously with, or after the other metallic components are added to the carrier material. Ordinarily, best results are obtained when this component is impregnated simultaneously with the other metallic components of the composite. Likewise, best results are ordinarily obtained when the tin or lead component is tin oxide.

Regardless of which tin or lead compound is used in the preferred impregnation step, it is essential that the tin or lead component be uniformly distributed throughout the carrier material. In order to achieve this objective when this component is incorporated by impregnation, it is necessary to maintain the pH of the impregnation solution at a relatively low level corresponding to about 7 to about 1 or less and to dilute the impregnation solution to a volume which is at least approximately the same or greater than the void volume of the carrier material which is impregnated. It is preferred to use a volume ratio of impregnation solution to carrier material of at least 1:1 and preferably about 2:1 to about 10:1 or more. Similarly, it is preferred to use a relatively long contact time during the impregnation step ranging from about ¼ hour up to about ½ hour or more before drying to remove excess solvent in order to insure a high dispersion of the tin or lead component in the carrier material. The carrier material is, likewise preferably constantly agitated during this preferred impregnation step.

A second essential ingredient of the subject catalyst is the platinum or palladium component. That is, it is intended to cover the use of platinum or palladium or mixtures thereof as a second component of the present composite. It is an essential feature of the present invention that substantially all of this platinum or palladium component exists within the final catalytic composite in the elemental metallic state. Generally, the amount of this component present in the final catalyst composite is small compared to the quantities of the other components combined therewith. In fact, the platinum or palladium component generally will comprise about 0.01 to about 2 wt. % of the final catalytic composite, calculated on an elemental basis. Excellent results are obtained when the catalyst contains about 0.05 to about 1 wt. % of platinum or palladium metal.

This platinum or palladium component may be incorporated in the catalytic composite in any suitable manner known to result in a relatively uniform distribution of this component in the carrier material such as coprecipitation or cogellation, ion exchange, or impregnation. The preferred method of preparing the catalyst involves the utilization of a soluble, decomposable compound of platinum of palladium to impregnate the carrier material in a relatively uniform manner. For example, this component may be added to the support by commingling the latter with an aqueous solution of chloroplatinic or chloropalladic acid. Other water-soluble compounds of platinum or palladium may be employed in impregnation solutions and include ammonium chloroplatinate, bromoplatinic acid, platinum dichloride, platinum tetrachloride hydrate, platinum dichlorocarbonyl dichloride, dinitrodiamino-platinum, palladium chloride, palladium nitrate, palladium sulfate, tetrammine palladium (II) chloride, etc. The utilization of a platinum or palladium chloride compound, such as chloroplatinic or chloropalladic acid, is ordinarily preferred. Nitric acid or hydrogen chloride or the like acid is also generally added to the impregnation solution in order to further facilitate the uniform distribution of the metallic component throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

Yet another essential ingredient of the present catalytic composite is an iridium component. It is of fundamental importance that substantially all of the iridium component exists within the catalytic composite of the present invention in the elemental state and the subsequently described reduction procedure is designed to accomplish this objective. The iridium component may be utilized in the composite in any amount which is catalytically effective, with the preferred amount being about 0.01 to about 2 wt. % thereof, calculated on an elemental iridium basis. Typically best results are obtained with about 0.05 to about 1 wt. % iridium. It is, additionally, preferred to select the specific amount of iridium from within this broad weight range as a function of the amount of the platinum or palladium component, on an atomic basis, as is explained hereinafter.

This iridium component may be incorporated into the catalytic composite in any suitable manner known to those skilled in the catalyst formulation art which results in a realtively uniform dispersion of iridium in the carrier material. In addition, it may be added at any stage of the preparation of the composite—either during preparation of the carrier material or thereafter—and the precise method of incorporation used is not deemed to be critical. However, best results are obtained when the iridium component is relatively uniformly distributed throughout the carrier material, and the preferred procedures are the ones known to result in a composite having this relatively uniform distribution. One acceptable procedure for incorporating this component into the composite involves cogelling or coprecipitating the iridium component during the preparation of the preferred carrier material, alumina. This procedure usually comprehends the addition of a soluble, decomposable compound of iridium such as chloroiridic acid or iridium tetrachloride to the alumina hydrosol before it is gelled. The resulting mixture is then finished by conventional gelling, aging, drying, and calcination steps as explained hereinbefore. A preferred way of incorporating this component is an impregnation step wherein the porous carrier material is impregnated with a suitable iridium-containing solution either before, during, or after the carrier material is calcined. Preferred impregnation solutions are aqueous solutions of water soluble, decomposable iridium compounds such as rodium hexachloroiridate (IV), iridium tribromide, iridium dichloride, iridium tetrachloride, iridium oxalic acid, iridium sulfate, potassium iridichloride, chloroiridic acid, sodium hexonitroiridate (II), and the like compounds. Best results are ordinarily obtained when the impregnation solution is an aqueous solution of chloroiridic acid or sodium chloroiridate. This component can be added to the carrier material, either prior to, simultaneously with or after the other metallic components are combined therewith. Best results are usually achieved when this component is added simultaneously with the platinum or palladium components.

Yet another essential ingredient of the catalyst used in the present invention is the alkali or alkaline earth component. More specifically, this component is selected from the group consisting of the compounds of the alkali metals—cesium, rubidium, potassium, sodium, and lithium—and of the alkaline earth metals—calcium, strontium, barium, and magnesium. This component exists within the catalytic composite in an oxidation state above that of the elemental metal such as a relatively stable compound such as the oxide or sulfide, or in combination with one or more of the other components of the composite, or in combination with the carrier material such as, for example, in the form of a metal aluminate. Since, as is explained hereinafter, the composite containing the alkali or alkaline earth is always calcined in an air atmosphere before use in the conversion of hydrocarbons, the most likely state this component exists in during use in the dehydrogenation reaction is the corresponding metallic oxide such as lithium oxide, potassium oxide, sodium oxide, and the like. Regardless of what precise form in which it exists in the composite, the amount of this component utilized is preferably selected to provide a nonacidic composite containing about 0.1 to about 5 wt. % of the alkali or alkaline earth metal, and, more preferably, about 0.25 to about 3.5 wt. %. Best results are obtained when this component is a compound of lithium or potassium. The function of this component is to neutralize any of the acidic material which may have been used in the preparation of the present catalyst so that the final catalyst is nonacidic.

This alkali or alkaline earth component may be combined with the porous carrier material in any manner known to those skilled in the art to result in a relatively uniform dispersion of this component throughout the carrier material with consequential neutralization of any acidic sites which may be present therein. Typically good results are obtained when it is combined by impregnation, coprecipitation, ion-exchange, and the like procedures. The preferred procedure, however, involves impregnation of the carrier material either before, during, or after it is calcined, or before, during, or after the other metallic ingredients are added to the carrier material. Best results are ordinarily obtained when this component is added to the carrier material after the other metallic components because the alkali metal or alkaline earth metal acts to neutralize the acid used in the preferred impregnation procedure for these metallic components. In fact, it is preferred to add the platinum or palladium, iridium, and tin or lead components to the carrier material, oxidize the resulting composite in an air stream at a high temperature (i.e. typically about 600° to 1000° F.), then treat the resulting oxidized composite with steam or a mixture of air and steam in order to remove at least a portion of any residual acidity and thereafter add the alkali metal or alkaline earth component. Typically, the impregnation of the carrier material with this component is performed by contacting the carrier material with a solution of a suitable decomposable compound or salt of the desired alkali or alkaline earth metal. Hence, suitable compounds include the alkali metal or alkaline earth metal halides, sulfates, nitrates, acetates, carbonates, phosphates, and the like compounds. For example, excellent results are obtained by impregnating the carrier material after the platinum or palladium, iridium, and tin or lead components have been combined therewith, with an aqueous solution of lithium nitrate or potassium nitrate.

Regarding the preferred amounts of the various metallic components of the subject catalyst, I have found it to be a good practice to specify the amounts of the iridium component, the tin or lead component, and the alkali or alkaline earth component, as a function of the amount of the platinum or palladium component. On this basis, the amount of the iridium component is ordinarily selected so that the atomic ratio of iridium to platinum or palladium metal is about 0.1:1 to about 2:1, with the preferred range being about 0.25:1 to 1.5:1. Similarly, the amount of the tin or lead component is ordinarily selected to produce a composite having an atomic ratio of tin or lead to platinum or palladium metal within the broad range of about 0.05:1 to 10:1, the best practice is to select this ratio on the basis of the following preferred ranges: (1) for tin, it is about 0.1:1 to 3:1, with the most preferred range being about 0.5:1 to 1.5:1; and (2) for lead, it is about 0.05:1 to 0.9:1, with the most preferred range being about 0.1:1 to 0.75:1. Similarly, the amount of the alkali or alkaline earth component is ordinarily selected to produce a composite having an atomic ratio of alkali or alkaline earth metal to platinum or palladium metal of about 5:1 to about 50:1 or more, with the preferred range being about 10:1 to about 25:1.

Another significant parameter for the instant catalyst is the "total metals content" which is defined to be the sum of the platinum or palladium component, the iridium component, the tin or lead component, and the alkali or alkaline earth component, calculated on an elemental metal basis. Good results are ordinarily obtained with the subject catalyst when this parameter is fixed at a value of about 0.2 to about 5 wt. %, with best results ordinarily achieved at a metals loading of about 0.4 to about 4 wt. %.

Integrating the above discussion of each of the essential components of the catalytic composite used in the present invention, it is evident that a particularly preferred catalytic composite comprises a combination of a platinum component, an iridium component, a tin or lead component, and an alkali or alkaline earth component with an alumina carrier material in amounts sufficient to result in the composite containing from about 0.05 to about 1 wt. % platinum, about 0.05 to about 1 wt. % iridium, about 0.05 to about 2 wt. % of the tin or lead, and about 0.25 t about 3.5 wt. % of the alkali or alkaline earth metal.

Regardless of the details of how the components of the catalyst are combined with the porous carrier material, the resulting multimetallic composite generally will be dried at a temperature of about 200° F. to about 600° F. for a period of from about 2 to 24 hours or more, and finally calcined at a temperature of about 600° F. to about 1100°F. in an air atmosphere for a period of about 0.5 to 10 hours, preferably about 1 to about 5 hours, in order to convert substantially all the metallic components to the corresponding oxide form. When acidic components are present in any of the reagents used to effect incorporation of any one of the components of the subject composite, it is a good practice to subject the resulting composite to a high temperature treatment with steam or with a mixture of steam and air, either after or before the calcination step described above, in order to remove as much as possible of the undesired acidic component. For example, when the platinum or palladium component is incorporated by impregnating the carrier material with chloroplatinic acid, it is preferred to subject the resulting composite to a high temperature treatment with steam in order to remove as much as possible of the undesired chloride.

It is essential that the resultant multimetallic calcined catalytic composite be subjected to a substantially water-free reduction prior to its use in the conversion of hydrocarbons. This step is designed to insure a uniform and finely divided dispersion of the metallic components throughout the carrier material. Preferably, substantially pure and dry hydrogen (i.e. less than 20 vol. ppm $H_2O$) is used as the reducing agent in this step. The reducing agent is contacted with the calcined composite at a temperature of about 800° F. to about 1200° F., a gas hourly space velocity of about 100 to about 5,000 $hr.^{-1}$, and for a period of time of about 0.5 to 10 hours or more, effective to reduce at least substantially all of platinum or palladium and iridium components to the corresponding elemental metallic state while maintaining the tin or lead component in a positive oxidation state. This reduction treatment may be performed in situ as part of a start-up sequence if precautions are taken to predry the plant to a substantially water-free state and if substantially water-free hydrogen is used.

The resulting reduced multimetallic catalytic composite may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture containing a mole ratio of $H_2$ to $H_2S$ of about 10:1 at conditions sufficient to effect the desired incorporation of sulfur, generally including a temperature ranging from about 50° F. up to about 1100° F. or more. This presulfiding step can be performed in situ or ex-situ.

According to the method of the present invention, the dehydrogenatable hydrocarbon is contacted with the instant nonacidic multimetallic catalytic composite in a dehydrogenation zone at dehydrogenation conditions. This contacting may be accomplished by using the catalyst in a fixed bed system, a moving bed system, a fluidized bed system, or in a batch type operation; however, in view of the danger of attrition losses of the valuable catalyst and of well-known operation advantages, it is preferred to use a fixed bed system. In this system, the hydrocarbon feed stream is preheated by any suitable heating means to the desired reaction temperature and then passed into a dehydrogenation zone containing a fixed bed of the catalyst type previously characterized. It is, of course, understood that the dehydrogenation zone may be one or more separate reactors with suitable heating means therebetween to insure that the desired conversion temperature is maintained at the entrance to each reactor. It is also to be noted that the reactants may be contacted with the catalyst bed in either upward, downward, or radial flow fashion, with the latter being preferred. In addition it is to be noted that the reactants may be in the liquid phase, a mixed liquid-vapor phase, or a vapor phase when they contact the catalyst, with best results obtained in the vapor phase.

Although hydrogen is the preferred diluent for use in the subject dehydrogenation method, in some cases other art-recognized diluents may be advantageously utilized such as steam, methane, carbon dioxide, and the like diluents. Hydrogen is preferred because it serves the dual-function of not only lowering the partial pressure of the dehydrogenatable hydrocarbon, but also of suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of about 1.5:1 to about 10:1. The hydrogen stream charged to the dehydrogenation zone will typically be recycle hydrogen obtained from the effluent stream from this zone after a suitable separation step.

When hydrogen is used as the diluent, a preferred practice is to add water or a water-producing compound to the dehydrogenation zone. This water additive may be included in the charge stock, or in the hydrogen stream, or in both of these, or added independently of these. Ordinarily, it is preferred to inject the necessary water by saturating at least a portion of the input hydrogen stream with water. Good results are also obtained when a water-producing compound such as a $C_2$ to $C_8$ alcohol is added to the charge stock. Regardless of the source of the water, the amount of equivalent water added should be sufficient to maintain the total amount of water continuously entering the dehydrogenation zone in the range of about 50 to about 10,000 wt. ppm. of the charge stock, with best results obtained at a level corresponding to about 1500 to 5000 wt. ppm of the charge stock.

Concerning the conditions utilized in the process of the present invention, these are generally selected from the conditions well known to those skilled in the art for the particular dehydrogenatable hydrocarbon which is charged to the process. More specifically, suitable conversion temperatures are selected from the range of about 700° to about 1200° F., with a value being selected from the lower portion of this range for the more easily dehydrogenated hydrocarbons such as the long chain normal paraffins and from the higher portion of this range for the more difficultly dehydrogenated hydrocarbons such as propane, butane, and the like hydrocarbons. For example, for the dehydrogenation of $C_6$ to $C_{30}$ normal paraffins, best results are ordinarily obtained at a temperature of about 800° to about 950°F. The pressure utilized is ordinarily selected at a value which is as low as possible consistent with the maintenance of catalyst stability and is usually about 0.1 to about 10 atmospheres, with best results ordinarily obtained in the range of about .5 to about 3 atmospheres. In addition, a liquid hourly space velocity (calculated on the basis of the volume amount, as a liquid, of hydrocarbon charged to the dehydrogenation zone per hour divided by the volume of the catalyst bed utilized) is selected from the range of about 1 to about 40 hr.$^{-1}$, with best results for the dehydrogenation of long chain normal paraffins typically obtained at a relatively high space velocity of about 25 to 35 hr.$^{-1}$.

Regardless of the details concerning the operation of the dehydrogenation step, an effluent stream will be withdrawn therefrom. This effluent will contain unconverted dehydrogenatable hydrocarbons, hydrogen, and products of the dehydrogenation reaction. This stream is typically cooled and passed to a separating zone wherein a hydrogen-rich vapor phase is allowed to separate from a hydrocarbon-rich liquid phase. In general, it is usually desired to recover the unreacted dehydrogenatable hydrocarbon from this hydrocarbon-rich liquid phase in order to make the dehydrogenation process economically attractive. This recovery step can be accomplished in any suitable manner known to the art such as by passing the hydrocarbon-rich liquid phase through a bed of suitable adsorbent material which has the capability to selectively retain the dehydrogenated hydrocarbon contained therein or by contacting same with a solvent having a high selectivity for the dehydrogenated hydrocarbon or by a suitable fractionation scheme where feasible. In the case where the dehydrogenated hydrocarbon is a mono-olefin, suitable adsorbents having this capability are activated silica gel, activated carbon, activated alumina, various types of specially prepared molecular sieves, and the like adsorbents. In another typical case, the dehydrogenated hydrocarbons can be separated from the unconverted dehydrogenatable hydrocarbons by utilizing the inherent capability of the dehydrogenated hydrocarbons to enter into several well-known chemical reactions such as alkylation, oligomerization, halogenation, sulfonation, hydration, oxidation, and the like reactions. Irrespective of how the dehydrogenated hydrocarbons are separated from the unreacted hydrocarbons, a stream containing the unreacted dehydrogenatable hydrocarbons will typically be recovered from this hydrocarbon separation step and recycled to the dehydrogenation step. Likewise, the hydrogen phase present in the hydrogen separating zone will be withdrawn therefrom, a portion of it vented from the system in order to remove the net hydrogen make, and the remaining portion is typically recycled, through suitable compressing means, to the dehydrogenation step in order to provide diluent hydrogen therefor.

In a preferred embodiment of the present invention wherein long chain normal paraffin hydrocarbons are dehydrogenated to the corresponding normal mono-olefins, a preferred mode of operation of this hydrocarbon separation step involves an alkylation reaction. In this mode, the hydrocarbon-rich liquid phase withdrawn from the separating zone is combined wtth a stream containing an alkylatable aromatic and the resulting mixture passed to an alkylation zone containing a suitable highly acidic catalyst such as an anhydrous solution of hydrogen fluoride. In the alkylation zone the mono-olefins react with the alkylatable aromatic while the unconverted normal paraffins remain substantially unchanged. The effluent stream from the alkylation zone can then be easily separated, typically by means of a suitable fractionation system, to allow recovery of the unreacted normal paraffins. The resulting stream of unconverted normal paraffins is then usually recycled to the dehydrogenation of the present invention.

The following working examples are introduced to illustrate further the novelty, mode of operation, utility, and benefits associated with the dehydrogenation method and nonacidic multimetallic catalytic composite of the present invention. These examples are intended to illustrative rather than restrictive.

These examples are all performed in a laboratory scale dehydrogenation plant comprising a reactor, a hydrogen separating zone, a heating means, cooling means, pumping means, compressing means, and the like equipment. In this plant the feed stream containing the dehydrogenatable hydrocarbon is combined with a hydrogen stream and the resultant mixture heated to the desired conversion temperature, which refers herein to the temperature maintained at the inlet to the reactor. The heated mixture is then passed into contact with the catalyst which is maintained as a fixed bed of catalyst particles in the reactor. The pressures reported herein are recorded at the outlet from the reactor. An effluent stream is withdrawn from the reactor, cooled, and passed into the separating zone wherein a hydrogen gas phase separates from a hydrocarbon-rich liquid phase containing dehydrogenated hydrocarbons, unconverted dehydrogenatable hydrocarbons, and a minor amount of side products of the dehydrogenation reaction. A portion of the hydrogen-rich gas phase is recovered as excess recycle gas with the remaining portion being continuously recycled through suitable compressive means to the heating zone as described above. The hydrocarbon-rich liquid phase from the separating oone is withdrawn therefrom and subjected to analysis to determine conversion and selectivity for the desired dehydrogenated hydrocarbon as will be indicated in the examples. Conversion numbers of the dehydrogenatable hydrocarbon reported herein are all calculated on the basis of disappearance of the dehydrogenatable hydrocarbon and are expressed in mole percent. Similarly, selectivity numbers are reported on the basis of moles of desired hydrocarbon produced per 100 moles of dehydrogenatable hydrocarbon converted.

All of the catalysts utilized in these examples are prepared according to the following general method with suitable modifications in stoichiometry to achieve the compositions reported in each example. First, an alumina carrier material comprising 1/16 inch spheres is prepared by: forming an aluminum hydroxyl chloride sol by dissolving substantially pure aluminum pellets in a hydrochloric acid solution, adding hexamethylenetetramine to the sol, gelling the resulting solution by dropping it into an oil bath to form spherical particles of an alumina hydrogel, aging, and washing the resulting particles with an ammoniacal solution and finally drying, calcining, and steaming the aged and washed particles to form spherical particles of gamma-alumina containing substantially less than 0.1 wt. % combined chloride. Additional details as to this method of preparing this alumina carrier material are given in the teachings of U.S. Pat. No. 2,620,314.

Second, for the tin-containing catalyst examples, a properly selected amount of stannis chloride is dissolved in water. On the other hand, for the lead-containing catalyst examples, an aqueous solution of lead nitrate is used. An aqueous solution containing chloroplatinic acid, chloroiridic acid, and nitric acid is also prepared. The two solutions are then intimately admixed and used to impregnate the gamma-alumina particles. The amounts of the various reagents are carefully selected to yield final catalytic composite containing the hereinafter specified amounts of platinum, iridium, and tin or lead. In order to insure uniform distribution of metallic components throughout the carrier material, this impregnation step is performed by adding the alumina particles to the impregnation mixture with constant agitation. The impregnation mixture is maintained in contact with the alumina particles for a period of about ½ hour at a temperature of 70° F. thereafter, the temperature of the impregnation mixture is raised to about 225° F. and the excess solution is evaporated in a period of about 1 hour. The resulting dried particles are then subjected to a calcination treatment in an air atmosphere at a temperature of about 500 to about 1000° F. for about 2 to 10 hours effective to convert substantially all of the metallic components to the corresponding oxides. Thereafter, the resulting calcined particles are treated with an air stream containing from about 10 to 30% steam at a temperature of about 800° to about 1000° F. for an additional period from about 1 to about 5 hours in order to further reduce the residual combined chloride in the composite.

Finally, the alkali or alkaline earth metal component is added to the resulting calcined particles in a second impregnating step. This second impregnation step involves contacting the calcined particles with an aqueous solution of a suitable decomposable salt of the desired alkali or alkaline earth component. For the composites utilized in the present examples, the salt is either lithium nitrate or potassium nitrate. The amount of this salt is carefully chosen to result in a final nonacidic composite having the desired composition. The resulting alkali impregnated particles are then dried, calcined, and steamed in exactly the same manner as described above following the first impregnation step.

In all the examples the catalyst is reduced during start-up by contacting with hydrogen at an elevated temperature of about 900 to 1100° F. for a period of time sufficient to reduce substantially all of the platinum and iridium components to the elemental state while maintaining the other components in a positive oxidation state.

EXAMPLE I

The reactor is loaded with 100 cc's of a nonacidic catalyst containing, on an elemental basis, 0.375 wt. % platinum, 0.375 wt. % iridium, 0.2 wt. % tin, 0.5 wt. % lithium, and less than 0.15 wt. % chloride. The feed stream utilized is commercial grade isobutane containing 99.7 wt. % isobutane and 0.3 wt. % normal butane. The feed stream is contacted with the catalyst at a temperature of 1065° F., a pressure of 10 psig., a liquid hourly space velocity of 4.0 hr.$^{-1}$, a hydrogen to hydrocarbon mole ratio of 2:1. The dehydrogenation plant is lined-out at these conditions and a 20 hour test period commenced. The hydrocarbon product stream from the plant is continuously analyzed by GLC (gas-liquid chromotography) and a high conversion of isobutane is observed with good selectivity for isobutylene.

EXAMPLE II

The nonacidic catalyst contains, on an elemental basis, 0.25 wt. % platinum, 0.1 wt. % lead, 0.25 wt. % iridium, 0.5 wt. % lithium, and less than 0.15 wt. % combined chloride. The feed stream is commercial grade normal dodecane. The dehydrogenation reactor is operated at a temperature of 870° F., a pressure of 10 psig., a liquid hourly space velocity of 32 hr.$^{-1}$, and a hydrogen to hydrocarbon mole ratio of 8:1. After a line-out period, a 20 hour test period is performed during which the average conversion of the normal dodecane is maintained at a high level with a selectivity for dodecene of above 90%.

EXAMPLE III

The nonacidic catalyst is the same as utilized in Example II. The feed stream is normal tetradecane. The conditions utilized are a temperature of 840° F., a pressure of 20 psig., a liquid hourly space velocity of 32 hr.$^{-1}$, and a hydrogen to hydrocarbon mole ratio of 8:1. After a line-out period, a 20 hour test shows an average conversion of approximately 12% and a selectivity for tetradecene of above about 90%.

EXAMPLE IV

The nonacidic catalyst contains, on an elemental basis, 0.2 wt. % platinum, 0.2 wt. % iridium, 0.2 wt. % tin, and 0.6 wt. % lithium, with combined chloride being less than 0.2 wt. %. The feed stream is substantially pure normal butane. The conditions utilized are a temperature of 950° F., a pressure of 15 psig., a liquid hourly space velocity of 4.0 hr.$^{-1}$, and a hydrogen to a hydrocarbon mole ratio of 4:1. After a line-out period, a 20 hour test is performed and excellent conversion of the normal butane to butene is observed.

EXAMPLE V

The nonacidic catalyst contains, on an elemental basis, 0.375 wt. % platinum, 0.375 wt. % iridium, 0.2 wt. % tin, 2.8 wt. % potassium, and less than 0.2 wt. % combined chloride. The feed stream is commercial grade ethylbenzene. The conditions utilized are a pressure of 15 psig., a liquid hourly space velocity of 32 hr$^{-1}$, a temperature of 950° F., and a hydrogen to hydrocarbon mole ratio of 8:1. During a 20 hour test period, at least 85% of equilibrium conversion of ethylbenzene is observed with high selectivity for styrene.

It is intended to cover by the following claims all changes and modifications of the above disclosure of the present invention that would be self-evident to a man of ordinary skill in the catalyst formulation art or in the hydrocarbon dehydrogenation art.

I claim as my invention:

1. A method for dehydrogenating a dehydrogenatable hydrocarbon comprising contacting the hydrocarbons at dehydrogenating conditions with a nonacidic catalytic composite comprising a porous carrier material containing, on an elemental basis, about 0.01 to about 2 wt. % platinum or palladium, about 0.01 to 2 wt. % iridium, about 0.01 to about 5 wt. % tin or lead, and about 0.1 to about 5 wt. % of an alkali or alkaline earth metal, wherein the platinum or palladium, iridium, tin or lead, and alkali or alkaline earth metal are uniformly dispersed throughout the porous carrier material, wherein substantially all of the platinum or palladium and iridium are present in the corresponding elemental metallic state, wherein substantially all of the tin or lead is present in an oxidation state above that of the elemental metal, wherein substantially all of the alkali or alkaline earth metal is present in an oxidation state above that of the elemental metal, and wherein the atomic ratio of tin or lead to platinum or palladium is about 0.05:1 to about 10:1, wherein the atomic ratio of iridium to platinum or palladium is about 0.1:1 to about 2:1 and wherein the atomic ratio of the alkali or alkaline earth metal to platinum or palladium is about 5:1 to 50:1.

2. A method as defined in claim 1 wherein the porous carrier material is a refractory inorganic oxide.

3. A method as defined in claim 2 wherein the refractory inorganic oxide is alumina.

4. A method as defined in claim 1 wherein the alkali or alkaline earth metal is lithium.

5. A method as defined in claim 1 wherein the alkali or alkaline earth metal is potassium.

6. A method as defined in claim 1 wherein the composite contains, on an elemental basis, about 0.05 to about 1 wt. % platinum or palladium, about 0.05 to 1 wt. % iridium, about 0.05 to about 2 wt. % tin, and about 0.25 to about 3.5 wt. % alkali or alkaline earth metal and wherein the porous carrier material is alumina.

7. A method as defined in claim 1 wherein the dehydrogenatable hydrocarbon is admixed with hydrogen when it contacts the catalytic composite.

8. A method as defined in claim 1 wherein the dehydrogenatable hydrocarbon is an aliphatic compound containing 2 to 30 carbon atoms per molecule.

9. A method as defined in claim 1 wherein the dehydrogenatable hydrocarbon is a normal paraffin hydrocarbon containing about 4 to 30 carbon atoms per molecule.

10. A method as defined in claim 1 wherein the dehydrogenatable hydrocarbon is a normal paraffin hydrocarbon containing about 10 to about 18 carbon atoms per molecule.

11. A method as defined in claim 1 wherein the dehydrogenatable hydrocarbon is an alkylaromatic, the alkyl group of which contains 2 to 6 carbon atoms.

12. A method as defined in claim 1 wherein the dehydrogenatable hydrocarbon is a naphthene.

13. A method as defined in claim 1 wherein the dehydrogenation conditions include a temperature of about 700° to about 1200° F., a pressure of about 0.1 to about 10 atmospheres, a liquid hourly space velocity of about 1 to 40 hr.$^{-1}$, and a hydrogen to hydrocarbon mole ratio of about 1:1 to about 20:1.

14. A method as defined in claim 1 wherein substantially all of the tin or lead is in oxide form.

* * * * *